US011173275B2

(12) United States Patent
Sakaguchi

(10) Patent No.: US 11,173,275 B2
(45) Date of Patent: Nov. 16, 2021

(54) CATHETER HOLDING TOOL

(71) Applicant: TERUMO KABUSHIKI KAISHA, Tokyo (JP)

(72) Inventor: Yuuki Sakaguchi, Fujinomiya (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 235 days.

(21) Appl. No.: 15/928,504

(22) Filed: Mar. 22, 2018

(65) Prior Publication Data

US 2018/0339128 A1 Nov. 29, 2018

(30) Foreign Application Priority Data

May 23, 2017 (JP) .............................. JP2017-101903

(51) Int. Cl.
*A61M 25/00* (2006.01)
*A61M 25/06* (2006.01)
*A61M 25/09* (2006.01)
*A61B 8/12* (2006.01)
*B65D 85/04* (2006.01)

(52) U.S. Cl.
CPC ............. *A61M 25/002* (2013.01); *A61B 8/12* (2013.01); *A61M 25/0662* (2013.01); *A61M 25/09* (2013.01); *B65D 85/04* (2013.01); *A61M 2025/0681* (2013.01)

(58) Field of Classification Search
CPC ............ A61M 25/002; A61M 25/0662; A61M 25/09; A61M 2025/0681; B65D 85/04; A61B 50/20; A61B 50/30; A61B 50/33; A61B 1/00144; A61B 8/12; A61B 8/445

USPC ........................................................ 206/364
See application file for complete search history.

(56) References Cited

U.S. PATENT DOCUMENTS

| 4,216,860 A | * | 8/1980 | Heimann | ............ | A61M 25/002 |
| | | | | | 206/364 |
| 2012/0172846 A1 | | 7/2012 | Nakamoto et al. | | |
| 2014/0110296 A1 | * | 4/2014 | Terzibashian | ....... | A61M 25/002 |
| | | | | | 206/438 |
| 2016/0073862 A1 | * | 3/2016 | Matsuno | ................ | A61B 50/20 |
| | | | | | 606/47 |

FOREIGN PATENT DOCUMENTS

WO WO 2011/033939 A1 3/2011

* cited by examiner

*Primary Examiner* — Andrew D Perreault
(74) *Attorney, Agent, or Firm* — Buchanan Ingersoll & Rooney PC

(57) ABSTRACT

A catheter holding tool for holding a catheter. The catheter holding tool includes an accommodation member. The accommodation member has a first accommodation portion which accommodates a first tubular portion and/or a second tubular portion of the catheter, a second accommodation portion which accommodates a second holding target portion of the catheter, and a holding portion which holds the second holding target portion when the second holding target portion is accommodated in the second accommodation portion. The catheter holding tool includes a fixing tool to fix the position of the first holding target portion. The fixing and unfixing of the position of the first holding target portion is independent of the holding portion of the accommodation member holding the second holding target portion of the catheter.

6 Claims, 7 Drawing Sheets

CATHETER HOLDING TOOL

CROSS-REFERENCES TO RELATED APPLICATIONS

This application claims priority to Japanese Application No. 2017-101903 filed on May 23, 2017, the entire content of which is incorporated herein by reference.

TECHNICAL FIELD

The present invention generally relates to a catheter holding tool.

BACKGROUND ART

An elongated medical instrument such as a catheter may be accommodated inside a predetermined container for easy handling and protection at the time of transportation or in a preparation stage before use. In addition, a certain catheter is accommodated inside a container in a state where the catheter is wound using a holding tool as disclosed in International Application Publication No. 2011/033939.

SUMMARY OF THE INVENTION

A catheter such as the one disclosed in International Application Publication No. 2011/033939 may include an elongated and flexible tubular portion(s) (sheath) and a relatively hard portion(s) (rigid portion) such as various connectors and a hub. In general, the order of detaching the flexible tubular portion, the connectors, and the hub is not particularly defined when the catheter is detached from (i.e., removed from) the container or the holding tool. For example, there may be a catheter with a rigid portion disposed on a proximal side of the tubular portion and another rigid portion disposed on a distal side of the tubular portion. In such a case, if the rigid portion (such as the connectors and the hub) disposed on the distal side of the tubular portion is unfixed first (i.e., before the rigid portion on the proximal side of the tubular portion is unfixed), unexpected deformation such as deflection occurs in the tubular portion extending between the respective rigid portions. Consequently, in some cases, an inadvertent force is applied to the tubular portion. This leads to a possibility that kink may occur in the tubular portion.

The catheter holding tool disclosed here is capable of preventing a kink from occurring in a flexible tubular portion when a catheter is detached from an accommodation member.

The catheter holding tool is for holding a catheter including a flexible first tubular portion, a first holding target portion that is disposed on a proximal side of the first tubular portion, and that is more rigid than the first tubular portion, a flexible second tubular portion that extends from the first holding target portion to the proximal side, and a second holding target portion that is disposed on the proximal side of the second tubular portion, and that is more rigid than the second tubular portion. The catheter holding tool includes an accommodation member that includes a first accommodation portion which accommodates the first tubular portion and/or the second tubular portion of the catheter, a second accommodation portion which accommodates the second holding target portion, and a holding portion which holds the second holding target portion in a state where the second holding target portion is accommodated in the second accommodation portion, and a fixing tool that fixes the first holding target portion in a state where the catheter is accommodated in the accommodation member. The holding portion is disposed integrally with the accommodation member. The fixing tool is capable of fixing and unfixing the first holding target portion of the catheter, independently of the holding portion of the accommodation member.

In another aspect, a catheter holding tool includes a catheter holder configured to hold a catheter. The catheter includes a distal tubular body, a distal relatively rigid member proximal to and connected to the distal tubular body, an intermediate tubular body proximal to and connected to the distal relatively rigid member, and a proximal relatively rigid member proximal to and connected to the intermediate tubular body. The distal relatively rigid member and the proximal relatively rigid member are more rigid that the distal tubular body and the intermediate tubular body. The catheter holder includes a first groove configured to hold the distal tubular body when the distal tubular body is wound and a second groove configured to hold the distal relatively rigid member, the intermediate tubular body and the proximal relatively rigid member of the catheter. The second groove integrally communicates with the first groove. The catheter holding tool includes a holding protrusion extending over a portion of the open top of the second groove to hold the proximal relatively rigid member within the second groove when the catheter is within the catheter holder. The holding protrusion is operable to release the proximal relatively rigid member from the second groove. The catheter holding tool further includes a fixing tool comprising a first clasp, a second clasp and an elongated extension body extending between the first clasp and the second clasp such that the first and second clasps are at opposite ends of the elongated extension body. The first clasp is configured to connect to the distal relatively rigid member and the second clasp is configured to connect to the distal tubular body. The first and second clasps of the fixing tool fix a position of the distal relatively rigid member relative to the distal tubular body when the first clasp is connected to the distal relatively rigid member and the second clasp is connected to the distal tubular body. The first and second clasps of the fixing tool are configured to fix and unfix the position of the distal relatively rigid member relative to the distal tubular body independently of the operating the holding protrusion to hold and release the proximal relatively rigid member from the second groove.

In yet another aspect, this disclosure involves a catheter storage device. The catheter storage device includes a catheter comprising a distal tubular body, a distal relatively rigid member proximal to and connected to the distal tubular body, an intermediate tubular body proximal to and connected to the distal relatively rigid member, and a proximal relatively rigid member proximal to and connected to the intermediate tubular body, the distal relatively rigid member and the proximal relatively rigid member being more rigid that the distal tubular body and the intermediate tubular body. The catheter storage device also includes a catheter holder holding the catheter. The catheter holder includes a first groove and a second groove, the distal tubular body of the catheter being wound and positioned in the first groove, the distal relatively rigid member, the intermediate tubular body and the proximal relatively rigid member collectively being positioned within the second groove, the second groove integrally communicating with the first groove, the first and second grooves of the catheter holder each possessing an open top and a bottom surface that holds respective portions of the catheter. The catheter storage device includes a holding protrusion extending over a portion of the open top of the second groove to hold the proximal relatively rigid member within the second groove. The holding protrusion is operable to release the proximal relatively rigid member from the second groove. The catheter storage device includes a fixing tool comprising a first clasp, a second clasp and an elongated extension body extending between the first clasp and the second clasp such that the first and second clasps are at opposite ends of the elongated extension body. The first clasp is directly connected to the distal relatively rigid member and the second clasp is connected to the distal tubular body to fix a position of the distal relatively rigid member relative to the distal tubular body. The fixing tool is operable to fix and unfix the position of the distal relatively rigid member relative to the distal tubular body independently of operating the holding protrusion to hold and release the proximal relatively rigid member from the second groove.

When the first tubular portion, the second tubular portion, and the second holding target portion of the catheter are detached from the accommodation member, the above-described catheter holding tool is maintained in a state where the first holding target portion of the catheter is fixed by the fixing tool. Therefore, if the user does not intentionally unfix the first holding target portion, the first holding target portion is less likely to be unfixed before the first tubular portion, the second tubular portion, and the second holding target portion (i.e., the first holding target portion is less likely to be unfixed first or at the same time as the first tubular portion, the second tubular portion, and the second holding target portion). Therefore, the user unconsciously carries out the work for unfixing the first holding target portion subsequent to detaching the first tubular portion, the second tubular portion, and the second holding target portion from the accommodation member. In this manner, it is possible to help prevent a kink from occurring in the second tubular portion when the catheter is detached from the accommodation member.

BRIEF DESCRIPTION OF THE DRAWINGS

FIG. 7A is a cross-sectional view illustrating a state where a first tubular portion is accommodated in a first accommodation portion, and FIG. 7B is a cross-sectional view illustrating a state where a liquid together with the first tubular portion is accommodated in the first accommodation portion.

DETAILED DESCRIPTION

Figure 1:
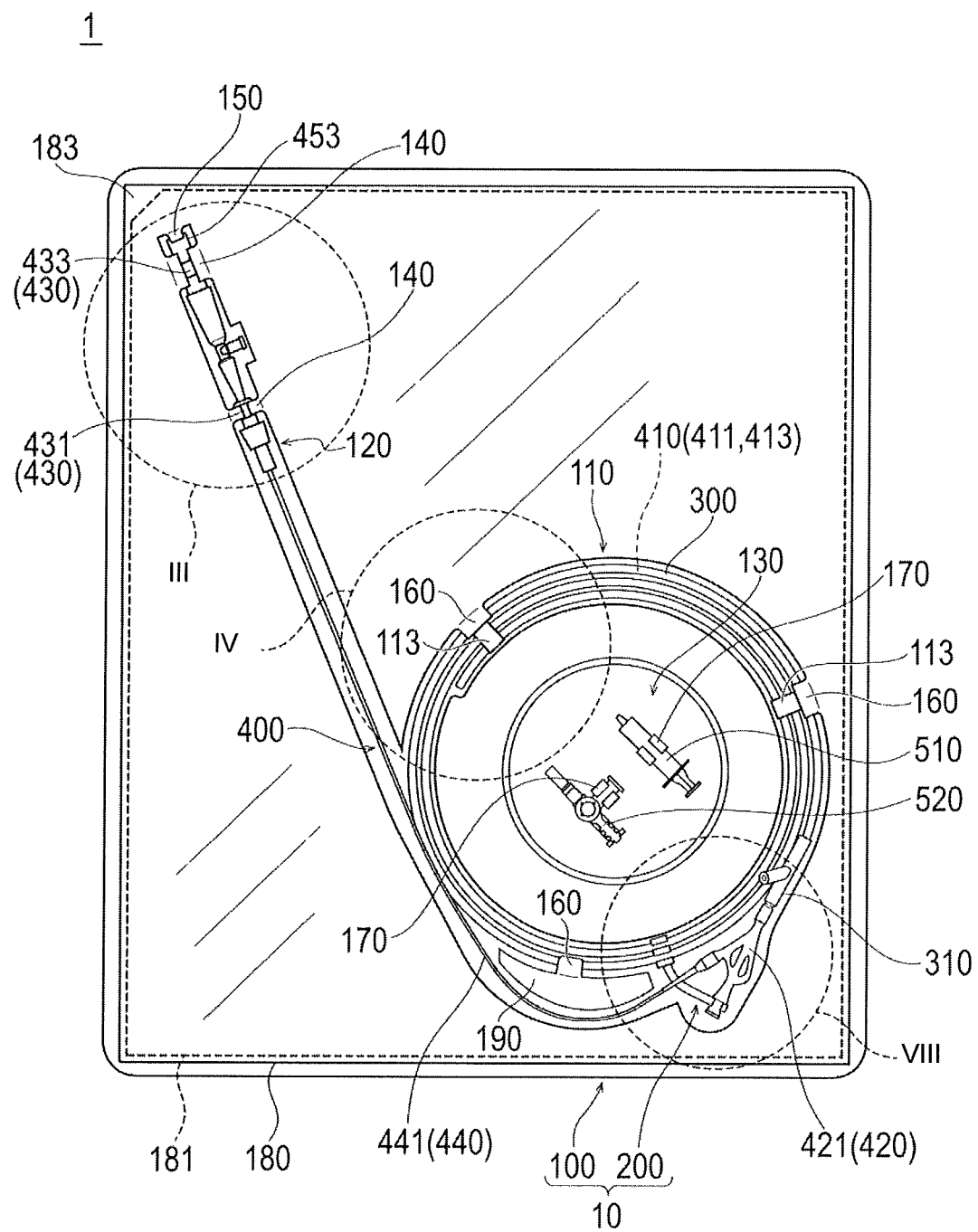
FIG. 1 is a plan view schematically illustrating a catheter set according to an embodiment.

Set forth below with reference to the accompanying drawings is a detailed description of embodiments of a catheter holding tool representing examples of the inventive catheter holding tool disclosed here. The following description does not limit the technical scope or definition of terms described in appended claims. The dimension ratios in the drawings may be exaggerated for convenience of description and different from the real dimension ratios.

Figure 2:
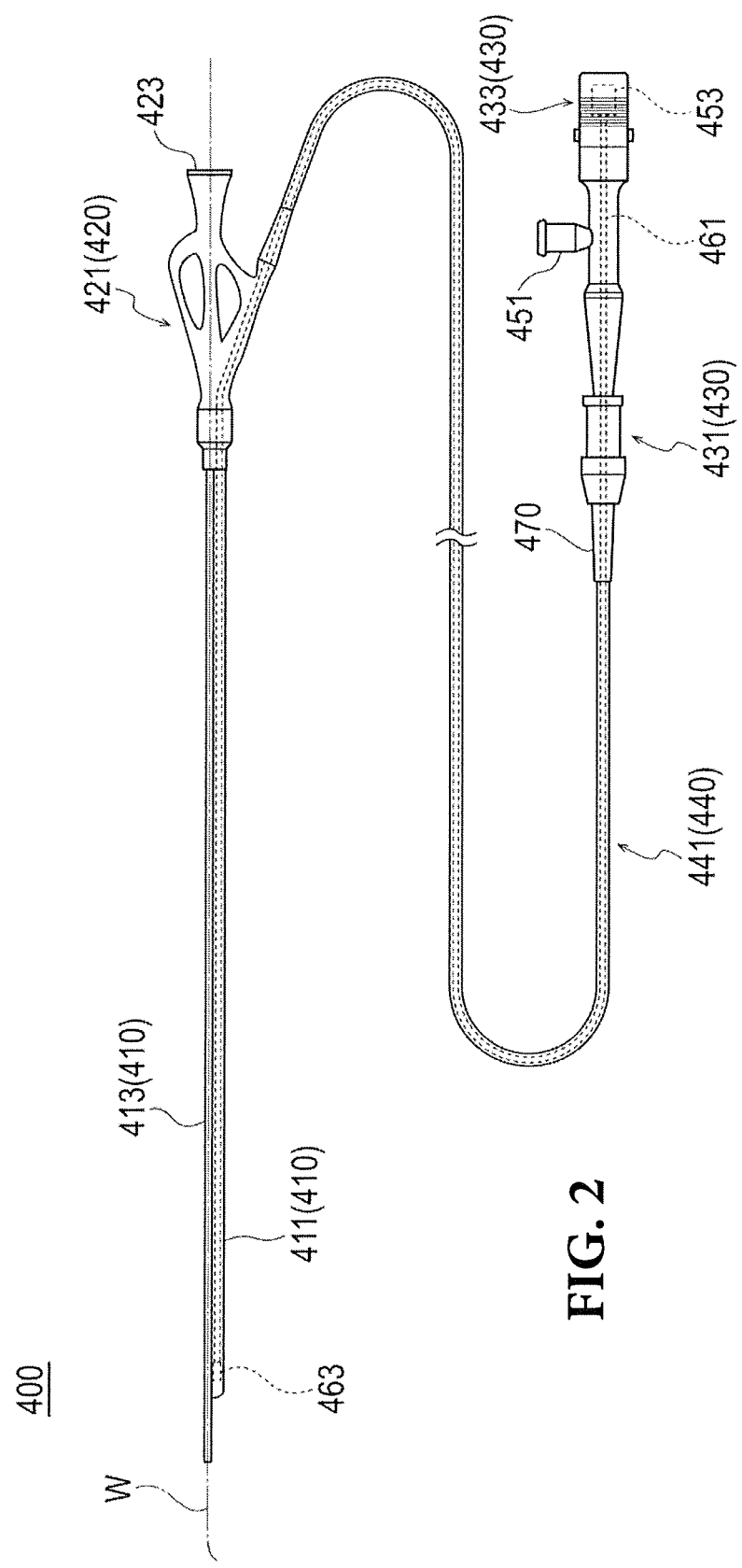
FIG. 2 is a view illustrating a catheter according to the embodiment.

FIG. 1 is a plan view schematically illustrating a catheter holding tool 10 according to the embodiment. FIG. 2 is a view illustrating an image diagnosis catheter 400 serving as a target held by the catheter holding tool 10. FIGS. 3 to 8 are views for describing each portion of the catheter holding tool 10. FIG. 9 is a view for describing a comparative example.

As illustrated in FIGS. 1 and 2, the catheter holding tool 10 according to the present embodiment is an instrument used to hold the image diagnosis catheter 400, which is for acquiring an image of a body lumen such as a blood vessel. The catheter holding tool 10 and the image diagnosis catheter 400 (i.e., when the image diagnosis catheter 400 is in a state of being held by the catheter holding tool 10) collectively configure a medical instrument set 1.

As illustrated in FIG. 1, the catheter holding tool 10 has an accommodation member 100, which accommodates the image diagnosis catheter 400, and a predetermined fixing tool 200.

The accommodation member 100 (i.e., a catheter holder) has a first accommodation portion 110, a second accommodation portion 120 and a holding portion 140. The first accommodation portion 110 accommodates a first tubular portion 410 of the image diagnosis catheter 400 in a wound state. The second accommodation portion 120 accommodates a second holding target portion 430 of the image diagnosis catheter 400, and the holding portion 140 holds the second holding target portion 430 in a state of being accommodated in the second accommodation portion 120.

The fixing tool 200 fixes the first holding target portion 420 of the image diagnosis catheter 400 in a state where the image diagnosis catheter 400 is accommodated in the accommodation member 100.

The holding portion 140 included in the accommodation member 100 is disposed integrally with the remaining components (e.g., the second accommodation portion 120) of the accommodation member 100. A user (e.g., a physician) carries out work for detaching (removing) the image diagnosis catheter 400 from the accommodation member 100. The configuration of the holding portion 140 allows the user to release the second holding target portion 430 held by the holding portion 140. Meanwhile, the fixing tool 200 is configured to fix and unfix the first holding target portion 420 of the image diagnosis catheter 400, independently of the holding portion 140 of the accommodation member 100. Accordingly, the first holding target portion 420 is satisfactory maintained fixed by the fixing tool 200 until the first holding target portion 420 fixed by the fixing tool 200 is unfixed separately from the work for detaching the image diagnosis catheter 400 from the accommodation member 100.

The image diagnosis catheter 400 will be described in more detail in relation to FIG. 2. In the present embodiment, a catheter dedicated to intravascular ultra sound (IVUS)

(which is configured to serve as a so-called over-the-wire type catheter) will be described as an example of the image diagnosis catheter 400. In describing the image diagnosis catheter 400, a configuration needed to describe the catheter holding tool 10 will be mainly described, and detailed description of the structure of the image diagnosis catheter 400 will be omitted.

The image diagnosis catheter 400 has an image sheath 411 including an image lumen into which a drive shaft 461 can be inserted, a guide wire sheath 413 including a guide wire lumen into which a guide wire W can be inserted and juxtaposed with the image sheath 411, and a hub portion 421 having a guide wire port 423 which communicates with the guide wire lumen, a connector portion (unit connector) 431 mechanically fixed to an external drive device. The image diagnosis catheter 400 also includes a proximal operation portion 433 disposed on a proximal side of the connector portion 431 and connected to the external drive device and a bendable and flexible tube 441 stretching between the hub portion 421 and the connector portion 431.

The image sheath 411 and the guide wire sheath 413 are welded (or bonded) integrally with each other. For example, the image sheath 411 and the guide wire sheath 413 can be integrated with each other in a state where the collective outer periphery of the image sheath 411 and guide wire sheath 413 is covered with a predetermined covering member 415 (as shown, for example, in FIG. 7A).

The image sheath 411 and the guide wire sheath 413 can be formed of a flexible material. The specific material is not particularly limited. For example, the material of the image sheath 411 and/or the guide wire sheath 413 may include various thermoplastic elastomers such as styrene-based, polyolefin-based, polyurethane-based, polyester-based, polyamide-based, polyimide-based, polybutadiene-based, trans polyisoprene-based, fluororubber-based, and chlorinated polyethylene-based elastomers. Among all of these materials, it is possible to use one or a combination of two or more materials (e.g., polymer alloy, polymer blend, or layered product).

An outer tube 470 interlocks with a distal side of the connector portion 431. An inner tube (not illustrated) is disposed inside the outer tube 470. The outer tube 470 and the inner tube form a dual tube structure which enables a pull-back operation of the drive shaft 461. A lumen of the inner tube communicates with the image lumen of the image sheath 411. In addition, the drive shaft 461 is inserted into the lumen of the inner tube.

The proximal operation portion 433 has a port 451 and a connector (joint) 453 (i.e., a proximal connector to connect to, for example, the external drive device). The drive shaft 461 is held within in the proximal operation portion 433.

The port 451 communicates with the image lumen of the image sheath 411. A priming syringe for supplying a priming solution and a Y-connector can be connected to the port 451 (i.e., the priming syringe can be connected to the port 451 via a Y-connector).

The connector 453 is configured to be connectable to a drive side connector (i.e., connector at the distal end) of the external drive device. The connector 453 and the drive side connector are connected to each other, thereby allowing the image diagnosis catheter 400 to be mechanically and electrically connected to the external drive device.

A distal portion of the drive shaft 461 has a transducer unit 463 which transmits and receives the ultrasound wave to and from a biological tissue of a living body to acquire image information when the transducer unit 462 is in the living body.

A signal line for transmitting a signal detected by the transducer unit 463 is disposed inside the drive shaft 461. When a diagnostic image of the body lumen (such as a blood vessel) is acquired, if rotational power is transmitted to the drive shaft 461, the transducer unit 463 rotates together with the drive shaft 461. In this manner, a lesion area inside the body lumen (such as the blood vessel) can be observed (imaged) in a circumferential direction.

Each of the hub portion 421, the connector portion 431, and the proximal operation portion 433 can be formed, for example, of a material which is more rigid than the image sheath 411, the guide wire sheath 413, and the flexible tube 441. A specific material of the hub portion 421, the connector portion 431, and the proximal operation portion 433 is not particularly limited. For example, the material of any of these components may be polyester such as polyvinyl chloride, polyethylene, polypropylene, cyclic polyolefin, polystyrene, poly-(4-methylpentene-1), polycarbonate, acrylic resin, acrylonitrile-butadiene-styrene copolymer, polyethylene terephthalate, and polyethylene naphthalate, or various resins such as butadiene-styrene copolymer, and polyamide (for example, nylon 6, nylon 66, nylon 610, nylon 12).

The distal portion of the flexible tube 441 interlocks with the hub portion 421, and the proximal portion of the flexible tube 441 interlocks with the outer tube 470 (i.e., the distal end of the flexible tube 441 is connected to the hub portion 421 and the proximal end of the flexible tube 441 is connected to the outer tube 470). The flexible tube 441 includes a lumen which communicates with the image lumen of the image sheath 411.

The flexible tube 441 is bendable and flexible. The distance and direction between the hub portion 421 and the connector portion 431 can thus be easily adjusted because the flexible tube 441 is bendable and flexible. For example, even when the image diagnosis catheter 400 is connected to the external drive device, the flexible tube 441 is appropriately extended so that a distance between an operator and other assisting operators can be adjusted. Accordingly, the image diagnosis catheter 400 and the external drive device do not interfere with each other during a medical procedure, thereby enabling treatment to be smoothly performed.

The flexible tube 441 can be formed of, for example, polyether ether ketone (PEEK) or a material which is the same as the example materials of the sheaths 411 and 413 described above.

The length of the flexible tube 441 extending in an axial direction of the flexible tube 441 is not particularly limited. The length can be, for example, 10 cm to 100 cm.

An example of using the catheter holding tool (the accommodation member 100 and the fixing tool 200) according to the present embodiment involves handling each portion of the image diagnosis catheter 400 as follows (referring to FIGS. 1 and 2).

The image sheath 411 and the guide wire sheath 413 of the image diagnosis catheter 400 can be handled as the first tubular portion 410 accommodated in a state of being wound around the first accommodation portion 110 of the accommodation member 100. In other words, the first accommodation portion 110 of the accommodation member 100 accommodates the image sheath 411 and the guide wire sheath 413 (collectively an example of a first tubular portion 410) of the image diagnosis catheter 400.

The hub portion 421 of the image diagnosis catheter 400 can be handled as the first holding target portion 420 serving as a target fixed by the fixing tool 200. In other words, the fixing tool 200 fixes the movement of the hub portion 421

(an example of a first holding target portion 420) of the image diagnosis catheter 400.

The connector portion 431 and the proximal operation portion 433 of the image diagnosis catheter 400 can be handled as the second holding target portion 430 serving as a target held by the holding portion 140 of the accommodation member 100. In other words, the holding portion 140 holds the connector portion 431 and the proximal operation portion 433 (collectively an example of the second holding target portion 430) of the image diagnosis catheter 400.

The flexible tube 441 of the image diagnosis catheter 400 can be handled as the second tubular portion 440 accommodated in the second accommodation portion 120 of the accommodation member 100. In other words, the second accommodation portion 120 holds the flexible tube 441 (an example of a second tubular portion 440) of the image diagnosis catheter 400.

Next, a configuration of each portion of the catheter holding tool 10 will be described.

Figure 3:
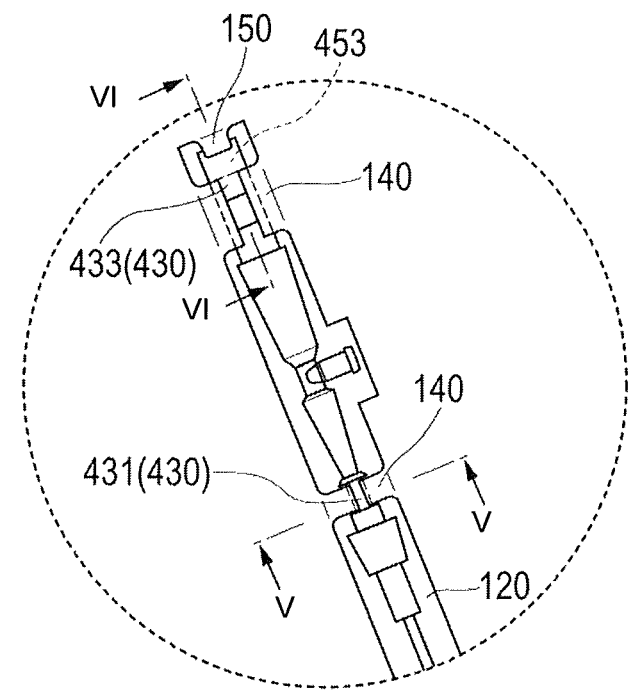
FIG. 3 is an enlarged view of a broken line portion III illustrated in FIG. 1.
Figure 5:
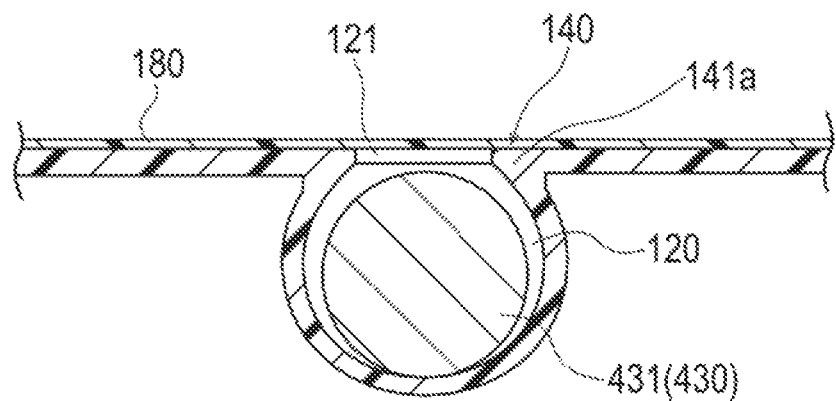
FIG. 5 is a cross-sectional view of an accommodation member which is taken along an arrow V-V illustrated in FIG. 3.

As illustrated in FIGS. 3 and 5, the second accommodation portion 120 of the accommodation member 100 has a concave cross-sectional shape (i.e., the bottom portion of the second accommodation portion 120 extends downward as shown in FIG. 5 to possess a concave cross-section) capable of accommodating (configured to accommodate) the second holding target portion 430 (the connector portion 431) of the image diagnosis catheter 400. The holding portion 140 of the accommodation member 100 has a claw portion 141a which prevents the second holding target portion 430 from being separated from the second accommodation portion 120.

The cross-sectional shape of the second accommodation portion 120 of the accommodation member 100 can be formed, for example, in a substantially curved U-shape as shown in FIG. 5. In addition, for example, the claw portion 141a included in the holding portion 140 can be formed in a convex shape which protrudes inward of the second accommodation portion 120 (toward the center of the second accommodation portion 120).

The inside of the claw portion 141a of the holding portion 140 has an opening portion 121 which can accommodate the second holding target portion 430 in the second accommodation portion 120 and can detach the second holding target portion 430 from the second accommodation portion 120. For example, a size (i.e., the dimension in a lateral direction illustrated in FIG. 5) of the opening portion 121 can be approximately the same as the size of the second holding target portion 430 in the lateral direction or can be shorter than the size of the second holding target portion 430. By forming the opening portion 121 in this way, it is possible to help prevent the second holding target portion 430 from being inadvertently separated from the second accommodation portion 120.

The cross-sectional shape of the second accommodation portion 120 and the claw portion 141a is not limited to the illustrated shape and can be appropriately changed. For example, a configuration may be adopted as follows. The holding portion 140 and the second accommodation portion 120 may be brought into close contact with the second holding target portion 430 in a state where the second holding target portion 430 is accommodated in the second accommodation portion 120 so that a predetermined fixing force is applied to the second holding target portion 430 by the second accommodation portion 120 and the holding portion 140. The fixing force applied to the second holding target portion 430 by the second accommodation portion 120 and the holding portion 140 can be formed to be weaker than the fixing force applied to the first holding target portion 420 (the hub portion 421) by the fixing tool 200. In this manner, it is possible to prevent the first holding target portion 420 from being unintentionally unfixed by the fixing tool 200 when the second holding target portion 430 is detached from the second accommodation portion 120.

The holding portion 140 (the claw portion 141a) which holds the proximal operation portion 433 serving as the second holding target portion 430 is configured similarly to the holding portion 140 which holds the above-described connector portion 431. Therefore, the description of the holding portion 140 holding the proximal operation portion 433 will be omitted.

Figure 6:
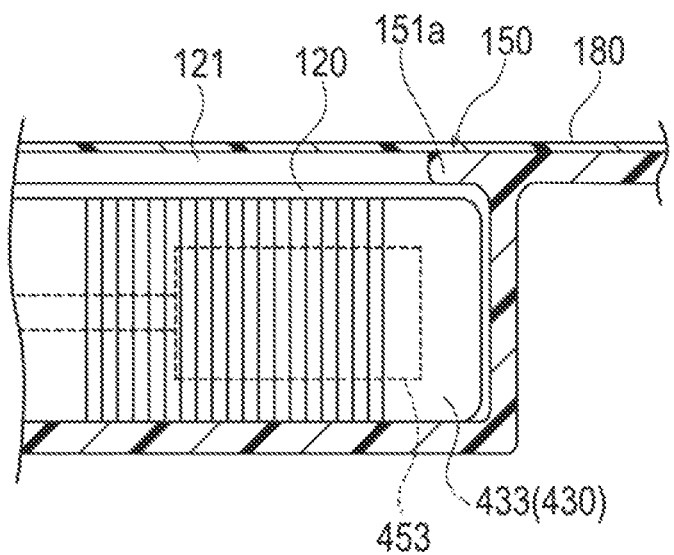
FIG. 6 is a cross-sectional view of the accommodation member which is taken along an arrow VI-VI illustrated in FIG. 3.

As illustrated in FIGS. 3 and 6, the accommodation member 100 has an auxiliary holding portion 150 which holds a state where the proximal end of the second holding target portion 430 (the proximal operation portion 433) is covered (i.e., the auxiliary holding portion 150 extends over the proximal end of the second holding target portion 430 to cover the radially outer surface of the proximal operation portion 433 as shown in FIG. 6).

As illustrated in FIG. 6, the auxiliary holding portion 150 has a claw portion 151a which protrudes toward the distal side from the proximal side of the proximal operation portion 433 (i.e., from the right side to the left side in FIG. 6). As described above, the proximal operation portion 433 of the image diagnosis catheter 400 has a connector 453 which is mechanically and electrically connectable to the external drive device. In addition, the connector 453 is connectable (i.e., configured to be connected) to the external drive device via an opening portion which opens to the proximal side of the proximal operation portion 433. The auxiliary holding portion 150 covers the proximal end of the proximal operation portion 433, thereby protecting the connector 453 disposed inside the proximal operation portion 433. Similarly to the holding portion 140, the auxiliary holding portion 150 can be configured to apply a fixing force to the proximal end of the proximal operation portion 433.

Figure 4:
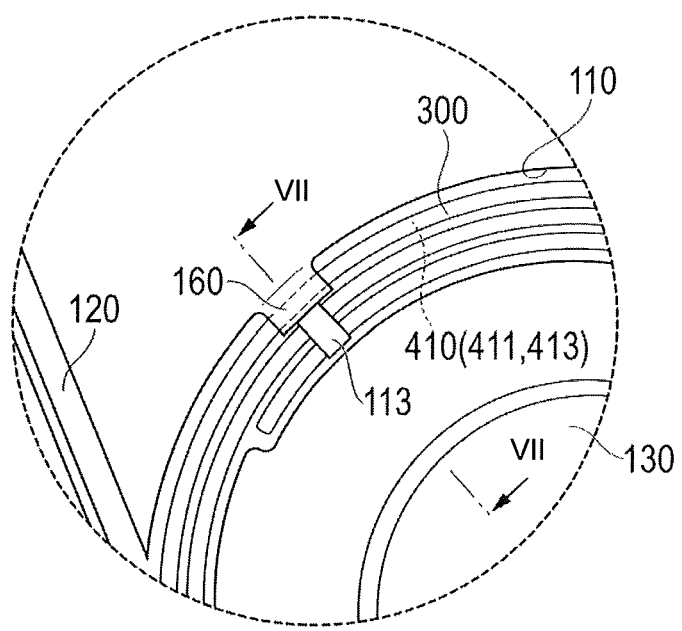
FIG. 4 is an enlarged view of a broken line portion IV illustrated in FIG. 1.
Figure 7A:
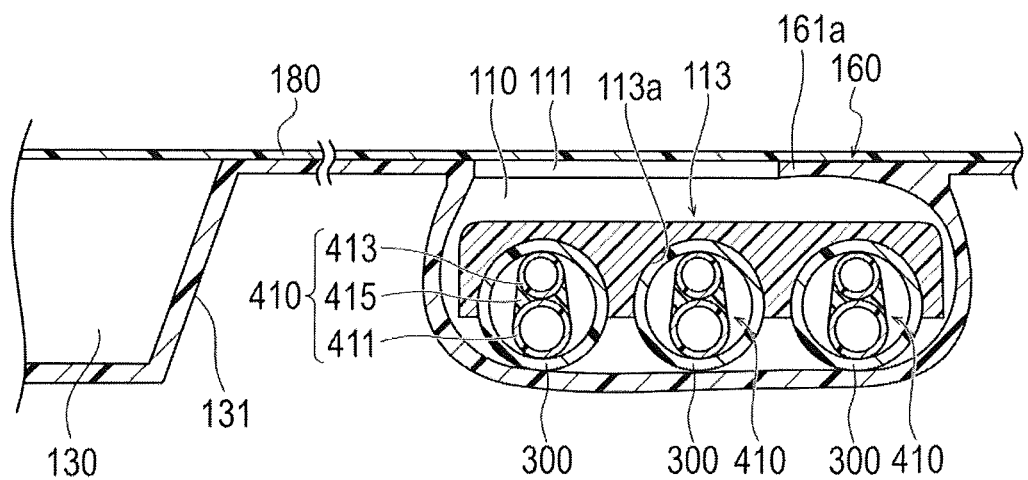
FIGS. 7A and 7B are cross-sectional views of the accommodation member taken along arrow VII-VII illustrated in FIG. 4.

As illustrated in FIGS. 4 and 7A, the first accommodation portion 110 of the accommodation member 100 has a concave cross-sectional shape which can accommodate the first tubular portion 410 (the image sheath 411 and the guide wire sheath 413) of the image diagnosis catheter 400.

As illustrated in FIG. 1, the first accommodation portion 110 (which accommodates the first tubular portion 410) and the second accommodation portion 120 (which accommodates a portion other than the first tubular portion 410, e.g., the first holding target portion 420, the second tubular portion 440, and the second holding target portion 430) of the accommodation member 100 are formed to be continuous with each other. Therefore, there is no clear boundary between the first accommodation portion 110 and the second accommodation portion 120. In order to clarify the boundary between the first accommodation portion 110 and the second accommodation portion 120, for example, it is possible to change a height (height position of a bottom surface of the concave portion) or a cross-sectional shape of the concave portion to indicate the boundary portion. FIG. 1 illustrates a predetermined partition portion 190 disposed in the second accommodation portion 120 so that the second tubular portion 440 (flexible tube 441) does not fluctuate (i.e., move uncontrollably) inside the second accommodation portion 120.

As illustrated in FIGS. 4 and 7(A), the first tubular portion 410 can be maintained in a state where the first tubular portion 410 is wound using a predetermined holding member 113 in a stage where the image diagnosis catheter 400 is not used (i.e., before the image diagnosis catheter 400 is removed from the accommodation member 100). For example, the holding member 113 can be configured to include a member including a snap fit mechanism (i.e., a clasp or clip) having a groove portion 113a fitted to the outer peripheral surface of the holder member 300 which accommodates the first tubular portion 410. Since the holding member 113 is used, it is possible to prevent the wound portions of the first tubular portion 410 from being overlapped or misaligned with each other.

An upper side (i.e., in the thickness direction of the first tubular portion 410) of the first accommodation portion 110 has a winding holding portion 160 which prevents the first tubular portion 410 from being separated from the first accommodation portion 110. The winding holding portion 160 has a claw portion 161a which protrudes inward of the first accommodation portion 110 (i.e., radially inward toward the center of the first accommodation portion 110). In addition, the upper side of the first accommodation portion 110 has an opening portion 111 which communicates with the first accommodation portion 110. The first tubular portion 410 can be moved into and out of the first accommodation portion 110 via the opening portion 111.

Figure 7B:
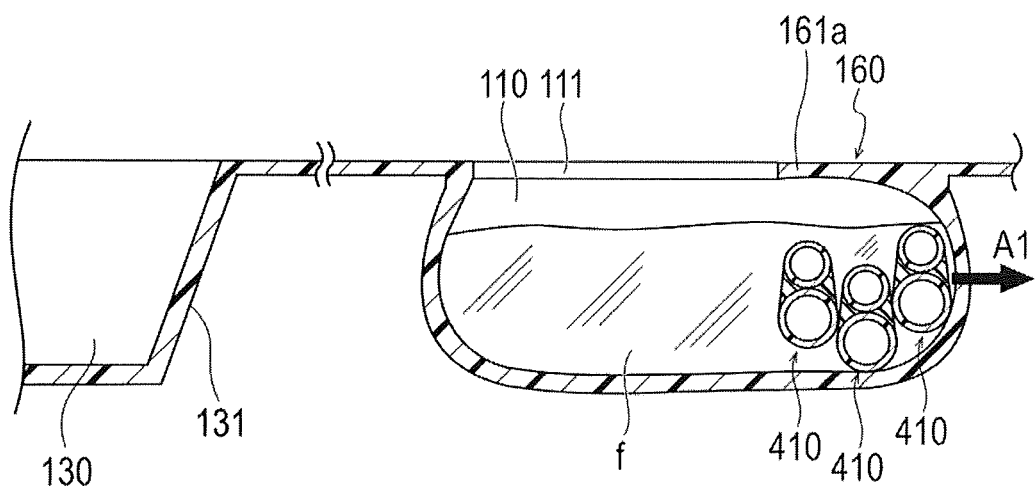

For example, the claw portion 161a can be formed only on the outer side (i.e., radially outer side) in the winding direction of the first tubular portion 410 (on the right side in FIGS. 7A and 7B). The opening portion 111 can be formed to be relatively large because the claw portion 161a is formed in this way (i.e., protruding radially inwardly from the radially outermost edge of the accommodation portion 110). Accordingly, the first tubular portion 410 (in a state of being wound by the holding member 113) is likely to be loaded to and unloaded from the first accommodation portion 110. In other words, the first accommodation portion 110 is configured to receive the first tubular portion 410 when the first tubular portion 410 is held in a wound position by the holding member 113 based on the above-described configuration.

As illustrated in FIG. 1, for example, in order to stably hold the first tubular portion 410, three winding holding portions 160 can be arranged at different positions along the winding direction of the first tubular portion 410. However, the position and the number of the winding holding portions 160 are not particularly limited.

As illustrated in FIG. 1 and FIG. 7A, the first tubular portion 410 is accommodated in the predetermined holder member (holder tube) 300 in a wound state before the image diagnosis catheter 400 is used. Any known member used for holding the catheter can be employed as the holder member 300.

FIG. 7B illustrates a state after the image diagnosis catheter 400 is inserted into a patient's body lumen. The first tubular portion 410 in this state is accommodated in the first accommodation portion 110 together with a liquid f (for example, a physiological salt solution). In this way, the first accommodation portion 110 is configured to be capable of holding the liquid (e.g., along with the first tubular portion 410).

The first accommodation portion 110 may be used, for example, as a liquid holding container (i.e., a vat) after the image diagnosis catheter 400 is temporarily removed from the body lumen. In this manner, it is possible to help prevent a generation of thrombus in the first tubular portion 410. It is possible to omit trouble (i.e., avoid extra procedural steps) needed to insert the first tubular portion 410 again into the holder member 300 in order to prevent the generation of thrombus in the first tubular portion 410. Therefore, the burden on the user (such as a physician) is reduced. In addition, the accommodation member 100 can be used as a liquid holding container dedicated to the image diagnosis catheter 400 during the medical procedure. Accordingly, the image diagnosis catheter 400 can be transported independently of the liquid holding container in which the guide wire or the balloon catheter is immersed. Therefore, it is possible to improve workability of the medical procedure using the image diagnosis catheter 400. In addition, the claw portion 161a is disposed in the first accommodation portion 110. Accordingly, even when the first tubular portion 410 is accommodated again in the first accommodation portion 110 after being temporarily detached from the first accommodation portion 110, it is possible to suitably prevent the first tubular portion 410 from being separated from the first accommodation portion 110.

As indicated by an arrow A1 in FIG. 7B, the first tubular portion 410 is deformed outward of the first accommodation portion 110 due to elasticity (flexibility) of the first tubular portion 410 if the first tubular portion 410 is not maintained in a wound state by the holding member 113. The claw portion 161a formed on the upper side of the first accommodation portion 110 prevents the first tubular portion 410 from projecting out of the opening portion 111 when the first tubular portion 410 is not maintained in a wound state. In this manner, it is possible to stably maintain a state where the first tubular portion 410 is accommodated inside the first accommodation portion 110.

For example, the first accommodation portion 110 and the winding holding portion 160 can be configured to apply a fixing force to the first tubular portion 410 or the holder member 300. In a case of this configuration, for example, the cross-sectional shape of the first accommodation portion 110 or the cross-sectional shape of the winding holding portion 160 can be appropriately changed. In this manner, the first tubular portion 410 and the holder member 300 are brought into close contact with each other. In addition, for example, a bottom portion of the first accommodation portion 110 can be formed to be thicker than the other portions (i.e., the bottom wall of the accommodation portion 110 is thicker than the other portions of the accommodation portion 110) so that the bottom of the accommodation portion does not fall out (i.e., break or rupture) when the liquid is accommodated. A thicker bottom portion of the first accommodation portion 110 also helps prevent the shape of the accommodation member 100 from inadvertently deforming due to the weight of the liquid.

As illustrated in FIGS. 1 and 7A, the accommodation member 100 has a third accommodation portion 130 which can accommodate medical instruments 510 and 520. The medical instruments 510 and 520 can be attached to the image diagnosis catheter 400. The third accommodation portion is formed on the inner side (i.e., radially inwards towards or at the center of the wound shape of the first tubular portion 410) of the accommodation member 100 relative to the first accommodation portion 110.

The medical instrument accommodated in the third accommodation portion 130, for example, may be a syringe 510 or a three-way stopcock 520. However, the type and the number of medical instruments are not particularly limited. For example, the medical instrument may include a medical needle.

The third accommodation portion 130 is provided with a medical instrument fixing portion 170 for fixing the syringe 510 or the three-way stopcock 520 as illustrated in FIG. 1. For example, the medical instrument fixing portion 170 can be configured to include a known snap fit mechanism.

As illustrated in FIGS. 7A and 7B, the third accommodation portion 130 is partitioned by a predetermined wall portion 131. Therefore, for example, the third accommodation portion 130 can be utilized as a container (vat) for holding liquid, similarly to the first accommodation portion 110 as described above. The cross-sectional shape of the third accommodation portion 130 is not particularly limited and can be appropriately changed.

The accommodation member 100 can be formed of a hard resin material such as ABS resin, polyethylene terephthalate, polymethyl methacrylate, and polycarbonate. In addition, the accommodation member 100 can be manufactured into a desired shape by using a manufacturing method such as vacuum molding or press molding using these materials.

Figure 8:
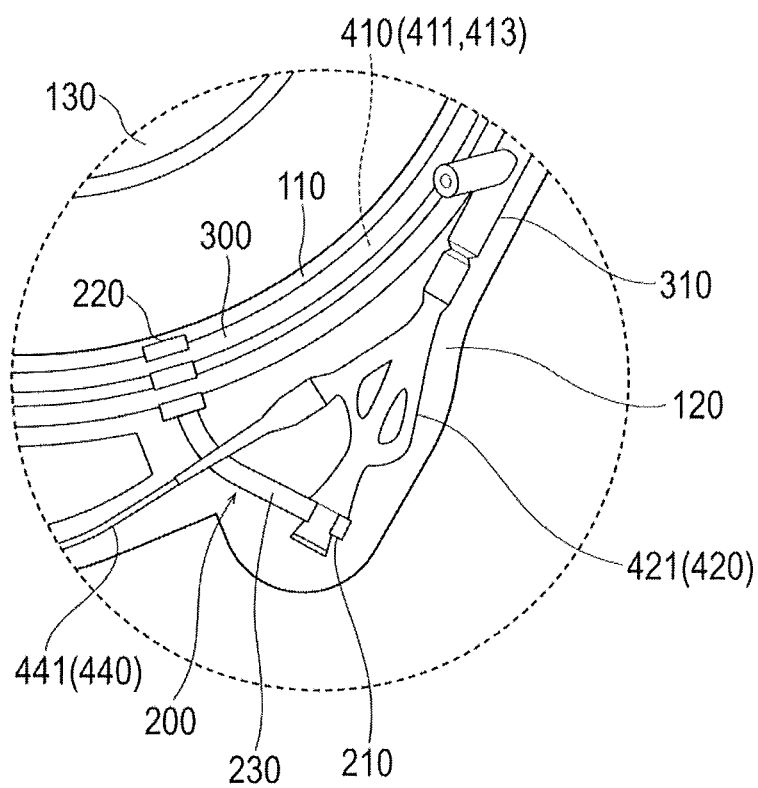
FIG. 8 is an enlarged view of a broken line portion VIII illustrated in FIG. 1.
Figure 9:
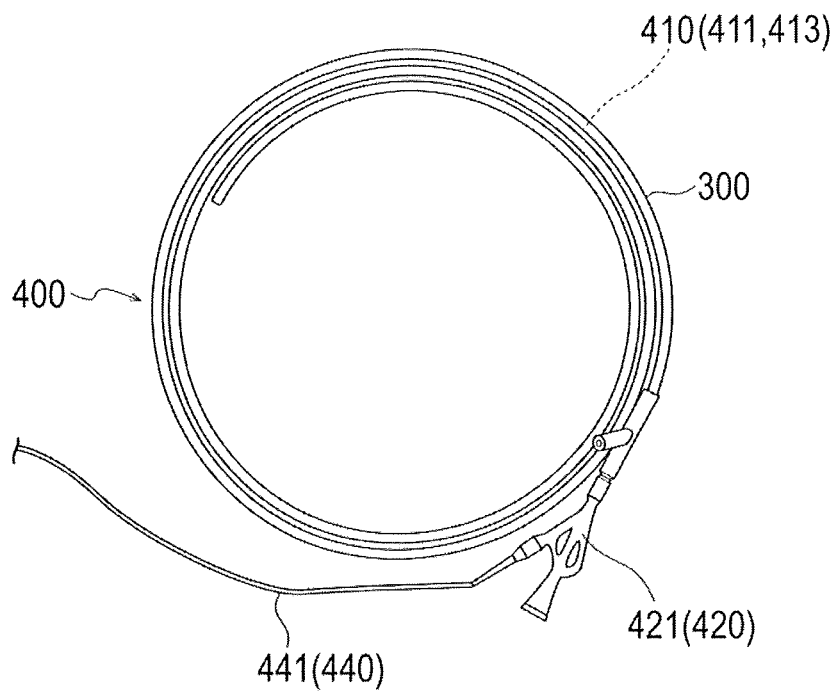
FIG. 9 is a view for describing a comparative example of the embodiment.

As illustrated in FIGS. 1 and 8, the fixing tool 200 has a first fixing portion 210 detachably fixed to the first holding target portion 420, a second fixing portion 220 detachably fixed to the holder member 300, and a main body portion 230 extending between the first fixing portion 210 and the second fixing portion 220.

For example, the first fixing portion 210 and the second fixing portion 220 of the fixing tool 200 can be configured to include a known snap fit mechanism. However, as long as each of the fixing portions 210 and 220 can generate a fixing force to fix/hold the position of the first holding target portion 420 of the image diagnosis catheter 400, the shape or the structure of the fixing portions 210 and 220 is not particularly limited.

For example, the fixing tool 200 can be formed of a hard resin material such as ABS resin, polyethylene terephthalate, polymethyl methacrylate, and polycarbonate, glass, or ceramics.

A port member 310 is attached to one end portion of the holder member 300. The port member 310 can be used in order to supply a flushing liquid into the holder member 300. The image diagnosis catheter 400 is insertable into the port member 310 from the distal side of the respective sheaths 411 and 413 and is thereby insertable into the holder member 300.

The accommodation member 100 and the fixing tool 200 can be covered with a film (for example, a porous membrane) 180 made of resin before the image diagnosis catheter 400 is used (e.g., during product shipment or transportation) as illustrated in FIG. 1. The film 180 is attached to form a sealing portion 181 which can be opened in a portion (i.e., at a position) other than the respective accommodating portions 110, 120, and 130 of the accommodation member 100. For example, the film 180 can be fixed to the accommodation member 100 to form the sealing portion 181 by means of welding or bonding. In addition, the film 180 is configured so that the film 180 can be gripped with fingers, and the film 180 has a grip portion 183 which forms an origin for detaching (opening) the film 180 as illustrated in FIG. 1.

When using the image diagnosis catheter 400, a user (e.g., a physician) first detaches the film 180. After the film 180 is detached, each portion of the image diagnosis catheter 400 remains accommodated in the respective accommodating portions 110 and 120 of the accommodation member 100. Accordingly, it is possible to prevent the image diagnosis catheter 400 from being inadvertently separated from the accommodation member 100.

Next, the user releases the second holding target portion 430 (the connector portion 431 and the proximal operation portion 433) held by the holding portion 140 integrally formed with the other portions of the accommodation member 100. In addition, the user releases the first tubular portion 410 (the image sheath 411 and the guide wire sheath 413) held by the winding holding portion 160 integrally formed with the other portions of the accommodation member 100. The first tubular portion 410 is released before, after or during (i.e., concurrently with) the releasing of the second holding target portion 430. After releasing the image diagnosis catheter 400 held by the respective holding portions 140 and 160, the user detaches the image diagnosis catheter 400 from the accommodation member 100.

While the above-described work (i.e., removal operations) is carried out, a state where the first holding target portion 420 is fixed by the fixing tool 200 is maintained. Therefore, if the user intentionally does not unfix the first holding target portion 420 before the image diagnosis catheter 400 held by the accommodation member 100 is released, the first holding target portion 420 remains fixed by the fixing tool 200 (i.e., the first holding target portion 420 is not inadvertently unfixed). Therefore, the user sequentially releases the image diagnosis catheter 400 held by the accommodation member 100 and then unfixes the first holding target portion 420 fixed by the fixing tool 200 without having to be concerned about unintended unfixing of the first holding target portion 420.

FIG. 9 illustrates a comparative example. When the second holding target portion 430 of the image diagnosis catheter 400 is fixed by the accommodation member 100 or another fixing tool as illustrated in FIG. 9, the flexible tube 441 extending between the first holding target portion 420 and the second holding target portion 430 may be bent so as to be greatly curved if the first holding target portion 420 (i.e., the portion fixed by the fixing tool 200 in FIG. 1) is unfixed. Leaving the first holding target portion 420 unfixed thus causes a possibility that a kink may occur in the flexible tube 441. In the catheter holding tool 10 according to the present embodiment, a user's work procedure is sequentially carried out so that the first holding target portion 420 and the second holding target portion 430 are held and unfixed a specific order (i.e., the second holding target portion 430 is unfixed first while the first holding target portion 420 continues to be fixed in place by the fixing tool 200). Accordingly, the possibility that a kink may occur in the flexible tube 441 is considerably reduced.

As described above, the catheter holding tool 10 according to the present embodiment has the accommodation member 100 including the first accommodation portion 110 (which accommodates the first tubular portion 410 of the image diagnosis catheter 400 in a wound state), the second accommodation portion 120 (which accommodates the second holding target portion 430 of the image diagnosis catheter 400), and the holding portion 140 (which holds the second holding target portion 430 in a state of being accommodated in the second accommodation portion 120), and the fixing tool 200 (which fixes the first holding target portion 420 of the image diagnosis catheter 400 in a state where the image diagnosis catheter 400 is accommodated in the accommodation member 100). The holding portion 140 is disposed integrally with the other portions of the accommodation member 100. The fixing tool 200 can fix and unfix the first holding target portion 420 of the image diagnosis catheter 400, independently of the fixing/unfixing by the holding portion 140 of the accommodation member 100.

In the catheter holding tool 10 configured as described above, when the first tubular portion 410, the second tubular portion 440, and the second holding target portion 430 of the image diagnosis catheter 400 are detached from the accommodation member 100, the fixing tool 200 maintains the first holding target portion 420 of the image diagnosis catheter 400 in a fixed state. Therefore, the first holding target portion 420 is less likely to be unintentionally unfixed first before the first tubular portion 410, the second tubular portion 440, and the second holding target portion 430 (unless the user intentionally unfixes the first holding target portion 420 first). Therefore, without having particular awareness of the work, the user (such as the physician) carries out the work for unfixing the first holding target portion 420, subsequent to the work for detaching the first tubular portion 410, the second tubular portion 440, and the second holding target portion 430 from the accommodation member 100. In this manner, when the image diagnosis catheter 400 is detached from the accommodation member 100, it is possible to prevent a kink from occurring in the second tubular portion 440.

In addition, the first accommodation portion 110 and the second accommodation portion 120 have a concave cross-sectional shape so that the first accommodation portion 110 and the second accommodation portion 120 can accommodate each portion of the image diagnosis catheter 400. The holding portion 140 includes the claw portion 141a which helps prevent the second holding target portion 430 from being separated from the second accommodation portion 120.

The accommodation member 100 is configured as described above. Accordingly, when the respective portions of the image diagnosis catheter 400 are accommodated in the first accommodation portion 110 and the second accommodation portion 120, it is possible to prevent the image diagnosis catheter 400 from being inadvertently separated from the accommodation member 100.

The accommodation member 100 includes the auxiliary holding portion 150, which covers the proximal end of the second holding target portion 430 to hold the proximal end of the second holding target portion 430. The auxiliary holding portion 150 can thus hold the second holding target portion 430 in a state where the proximal end (for example, the connector 453 disposed inside the proximal operation portion 433) of the second holding target portion 430 is protected.

The first accommodation portion 110 of the accommodation member 100 is configured to be capable of accommodating the liquid. Therefore, during the medical procedure using the image diagnosis catheter 400, the accommodation member 100 can be used as the liquid container. Accordingly, workability of the medical procedure using the image diagnosis catheter 400 can be improved.

The accommodation member 100 also includes the third accommodation portion 130 which can accommodate the medical instruments 510 and 520 that are attachable to the image diagnosis catheter 400. The third accommodation portion 130 is formed on the inner side of the accommodation member 100 relative to the first accommodation portion 110. Therefore, it is possible to effectively utilize the space present on the inner side (inner peripheral side) of the first accommodation portion 110. Accordingly, even though the medical instruments 510 and 520 are additionally held, it is possible to suppress an increase in an occupied area of the accommodation member 100.

The catheter holding tool 10 includes the holder member 300 which accommodates the first tubular portion 410 in a wound state. The fixing tool 200 is configured to be attachable to and detachable from the holder member 300. In the fixing tool 200 configured as described above, the holder member 300 and the first holding target portion 420 are fixed to each other. In this manner, it is possible to suitably prevent these two components from being misaligned relative to one another.

The first tubular portion 410 has the image sheath 411 (which includes the image lumen into which the drive shaft 461 of the image diagnosis catheter 400 can be inserted) and the guide wire sheath 413 (which includes the guide wire lumen into which the guide wire W can be inserted and juxtaposed with the image sheath). The first holding target portion 420 serves as the hub portion 421 having the guide wire port 423 which communicates with the guide wire lumen. In addition, the second holding target portion 430 has the connector portion 431 mechanically fixed to the external drive device and the proximal operation portion 433 disposed on the proximal side of the connector portion 431 and connectable to the external drive device. The second tubular portion 440 is a bendable and flexible tube 441 which stretches between the hub portion 421 and the connector portion 431. The holding portion 140 of the accommodation member 100 holds the connector portion 431 and the proximal operation portion 433.

The catheter holding tool 10 is configured to be capable of preventing a kink from occurring (i.e., kinking) in the flexible tube 441 of the image diagnosis catheter 400 having the above-described configuration. For this purpose, the catheter holding tool 10 is configured to sequentially release and unfix each portion of the image diagnosis catheter 400.

The catheter holding tool disclosed here has been described above with reference to the illustrated embodiment. The disclosed catheter holding tool is not limited to only the configuration of the described and illustrated embodiment. The disclosed catheter holding tool can be appropriately modified based on the scope of appended claims.

The accommodation member described in the embodiment is configured so that the second tubular portion (flexible tube) is accommodated in the second accommodation portion. However, for example, in a case where an effective length of the second tubular portion is relatively long, the second tubular portion may be accommodated in the first accommodation portion together with the first tubular portion in a wound state. In addition, for example, the first accommodation portion of the accommodation member may not be configured to accommodate the first tubular portion or the second tubular portion (or both of these) in a wound state. In other words, the first accommodation portion can be configured to accommodate the first tubular portion, the second tubular portion, or both in a substantially linearly extended state.

The accommodation member described above is configured to hold the catheter in two places of the connector portion (second holding target portion) and the proximal operation portion (second holding target portion). However, the accommodation member may be configured to hold the catheter in one place or more than two places.

Figure 10:
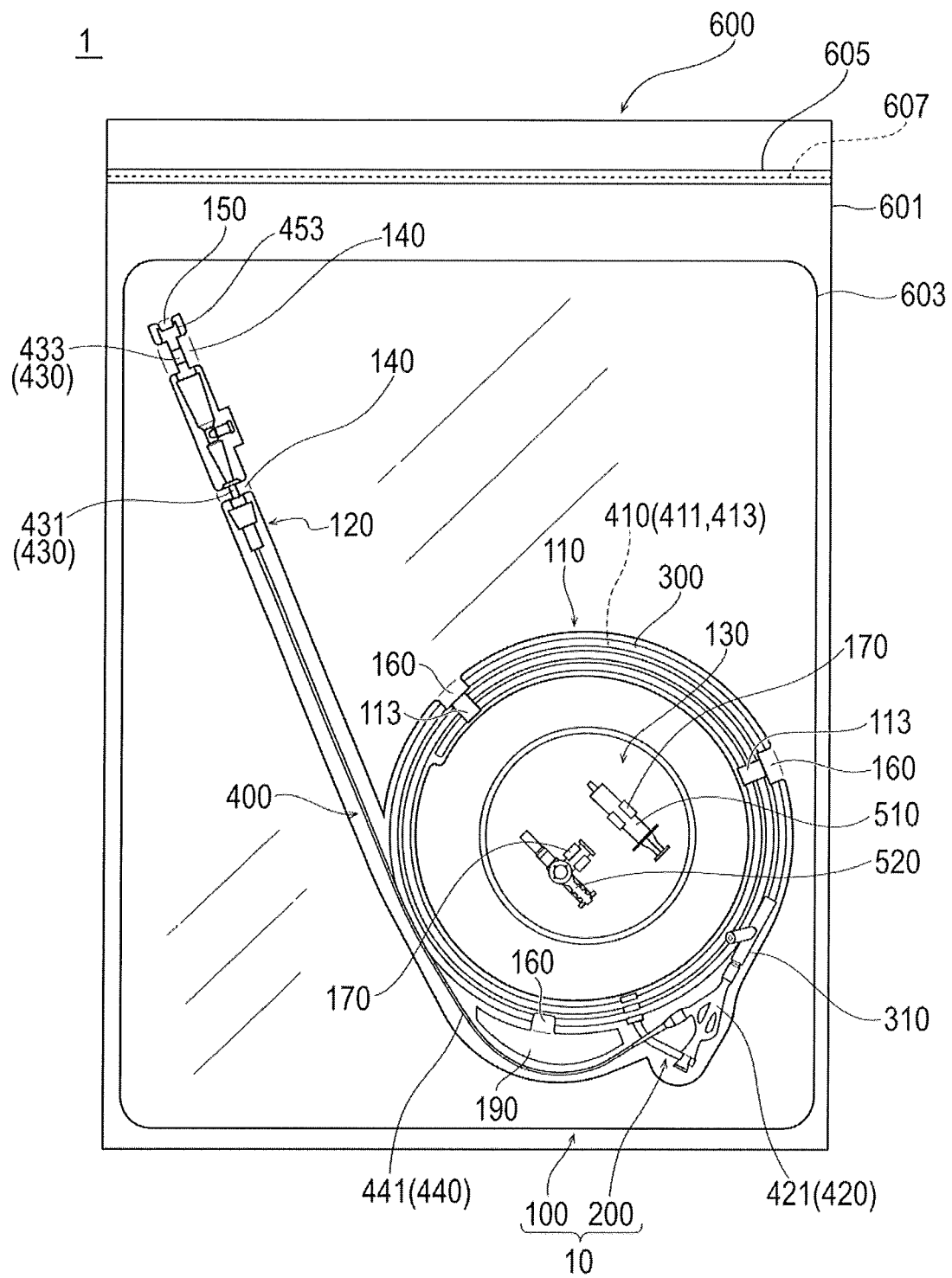
FIG. 10 is a plan view schematically illustrating a catheter set according to a modification example.

FIG. 10 illustrates a modification example in which the catheter 400 held by the catheter holding tool 10 may be accommodated in a predetermined package container 600. For example, as the package container 600, a peel bag generally used for packaging the medical instrument can be used. In the package container 600, a bag-shaped portion having a predetermined volume (shape) is partitioned by a pasteboard 601 configuring a base material of the package container 600 and a film portion 603 attached on the pasteboard 601. In addition, in order to maintain a state where the package container 600 is internally sterilized, the package container 600 includes an opening portion 605 formed on the upper side of the film portion 603, and a sealing portion 607 which seals the opening portion 605. For example, the pasteboard 601 can be formed of a gas permeable nonwoven fabric which enables ethylene oxide gas (EOG) sterilization in a state where the catheter is accommodated inside the package container 600.

An over-the-wire type ultrasound image diagnosis catheter including the flexible tube has been described as the catheter serving as the holding target of the catheter holding tool. However, the catheter is not limited to only this type. For example, the catheter holding tool can be used in conjunction with an over-the-wire type ultrasound image diagnosis catheter without including the flexible tube, a rapid exchange type ultrasound image diagnosis catheter, an optical coherence tomography catheter, a dual type image diagnosis catheter which includes the vascular ultrasonography catheter and the optical coherence tomography catheter and which can be used by switching the respective functions therebetween or at the same time, or an image diagnosis catheter using an optical frequency domain imaging method. In addition to the above-described catheters, the disclosed catheter holding tool is widely applicable to a catheter having a possibility of a problem that the kink may occur in the tubular portion (for example, the outer tube or the inner tube included in the image diagnosis catheter) corresponding to a curved tube when the curved tube is detached from the accommodation member.

The detailed description above describes a catheter holding tool and a catheter to be held by the catheter holding tool. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A catheter holding tool in combination with a catheter, the catheter comprising:
   a distal tubular body wound into a circular form, a distal relatively rigid member proximal to and connected to the distal tubular body, an intermediate tubular body proximal to and connected to the distal relatively rigid member, and a proximal relatively rigid member proximal to and connected to the intermediate tubular body, the distal relatively rigid member and the proximal relatively rigid member being more rigid that the distal tubular body and the intermediate tubular body;
   the catheter holding tool comprising:
     a catheter holder comprising a first groove in which are positioned adjacent windings of the distal tubular body that is wound into the circular form, the first groove being a continuous and circular first groove that holds an entirety of the distal tubular body that is wound into the circular form;
     the catheter holder comprising a second groove in which is positioned the distal relatively rigid member, the intermediate tubular body and the proximal relatively rigid member, the second groove being integral with and communicating with the first groove, the second groove being disposed outside the first groove, a part of the second groove projecting away from first groove, the second groove including a bottom wall, side walls extending upwardly from the bottom wall, and an open top that is open and that is positioned opposite the bottom wall of the second groove;
     a holding protrusion overlying a portion of the second groove at the open top of the second groove, the holding protrusion including a surface facing toward the bottom wall of the second groove and spaced from the bottom wall of the second groove to permit the proximal relatively rigid member to be positioned in the second groove by way of the open top, the holding protrusion overlying the proximal relatively rigid member in the second groove, the holding protrusion being configured to permit the proximal relatively rigid member to be removed from the second groove;
     a fixing tool comprising a first clasp, a second clasp and an elongated extension body extending between the first clasp and the second clasp such that the first and second clasps are spaced apart along the elongated extension body, the first clasp being connected to the distal relatively rigid member and the second clasp being connected to at least one of the adjacent windings of the distal tubular body that is wound into the circular form so that the distal relatively rigid member is fixed relative to the distal tubular body;
     the first and second clasps of the fixing tool fixing a position of the distal relatively rigid member relative to the distal tubular body;
     the fixing tool being separate from the catheter holder so that after removing the distal relatively rigid member and the distal tubular body from the second groove, the first clasp remains connected to the distal relatively rigid member and the second clasp remains connected to the distal tubular body so that the distal relatively rigid member remains fixed relative to the distal tubular body by the fixing tool; and
     the first and second clasps of the fixing tool being configured to fix and unfix the position of the distal relatively rigid member relative to the distal tubular body independently of the operating the holding protrusion to hold and release the proximal relatively rigid member from the second groove.

2. The catheter holding tool in combination with the catheter according to claim 1, wherein the holding protrusion overlying the portion of the second groove holding portion comprises two holding protrusions that both overlie the portion of the second groove, the two holding protrusions projecting towards one another but being spaced apart to define the open top of the second groove.

3. The catheter holding tool in combination with the catheter according to claim 1, wherein the holding protrusion is one holding protrusion that is spaced from a proximal-most end portion of the second groove toward the first groove so that the one holding protrusion is positioned between the proximal-most end portion of the second groove and the first groove, and further comprising an other holding protrusion at the proximal-most end portion of the second groove, the other holding protrusion covering a proximal end of the proximal relatively rigid member to hold the proximal end of the proximal relatively rigid member in the second groove.

4. The catheter holding tool in combination with the catheter according to claim 1, wherein a portion of the second groove that includes a proximal-most end portion of the second groove and the holding protrusion is linear.

5. The catheter holding tool in combination with the catheter according to claim 1, wherein the catheter holder comprises a medical instrument accommodation portion at which are positioned plural medical instruments each configured to be attached to the catheter, the medical instrument accommodation portion being positioned radially inwardly of the first groove so that the first groove surrounds the medical instrument accommodation portion, the medical instrument accommodation portion including a plurality of spaced apart medical instrument fixing parts that each fix in place one of the medical instruments.

6. The catheter holding tool in combination with the catheter according to claim 1, wherein the second groove includes a proximal-most end, a portion of the second groove that is farthest from the proximal-most end of the second groove being enlarged in a width dimension to accommodate the distal relatively rigid member.

* * * * *